United States Patent [19]
Hong et al.

[11] Patent Number: 6,028,067
[45] Date of Patent: Feb. 22, 2000

[54] CYCLOSPORIN-CONTAINING MICROEMULSION PRECONCENTRATE COMPOSITION

[75] Inventors: Chung Il Hong, East Amherst, N.Y.; Jung Woo Kim, Seoul, Rep. of Korea; Nam Hee Choi, Seoul, Rep. of Korea; Hee Jong Shin, Kyeonggi, Rep. of Korea; Su Geun Yang, Kyeonggi-do, Rep. of Korea

[73] Assignee: Chong Kun Dang Corp., Rep. of Korea

[21] Appl. No.: 09/067,363

[22] Filed: Apr. 27, 1998

[30] Foreign Application Priority Data

Dec. 5, 1997 [KR] Rep. of Korea ............ 97-66454
Mar. 24, 1998 [KR] Rep. of Korea ............ 98-10046

[51] Int. Cl.⁷ .................................................. A61K 31/545
[52] U.S. Cl. ........................... 514/200; 514/937; 514/951
[58] Field of Search .............................. 514/11, 937, 951, 514/200

[56] References Cited

U.S. PATENT DOCUMENTS

| | | | |
|---|---|---|---|
| 4,388,307 | 6/1983 | Cavanak | 424/177 |
| 5,342,625 | 8/1994 | Hauer et al. | 424/455 |
| 5,583,105 | 12/1996 | Kovacs et al. | 514/11 |
| 5,589,455 | 12/1996 | Woo | 514/11 |
| 5,603,951 | 2/1997 | Woo | 424/455 |
| 5,639,474 | 6/1997 | Woo | 424/452 |
| 5,639,724 | 6/1997 | Cavanak | 514/11 |
| 5,891,846 | 4/1999 | Ishida et al. | 514/11 |

FOREIGN PATENT DOCUMENTS

9522343  8/1995  WIPO .

*Primary Examiner*—Kevin E. Weddington
*Attorney, Agent, or Firm*—Heslin & Rothenberg, P.C.

[57] ABSTRACT

The present invention relates to a microemulsion preconcentrate composition comprising (1) cyclosporin as an active component; (2) alkyl ester of polycarboxylic acid and/or carboxylic acid ester of polyols as a lipophilic solvent; (3) oil; and (4) surfactant. The composition according to the present invention is characterized in that it dissolves in an external phase such as water, artificial gastric fluid and artificial intestinal fluid by controlling the mixing ratio of the components thereby to get the microemulsion form of inner phase diameter of 100 nm or below. The composition according to the present invention can be formulated as the dosage form of a soft capsule, a hard capsule sealed with a gelatin banding at the conjugated portion, or an oral liquid preparation for oral administration. Especially, if the cyclosporin microemulsion preconcentrate comprising cyclosporin, oil, lipophilic solvent and surfactant is formulated in a soft capsule according to the present invention, the resultant capsule removes the disadvantages of the prior arts showing the reactivity of hydrophilic solvent with gelatin shell of soft capsule and the volatility of hydrophilic solvent wherein the hydrophilic solvent was essential component in the composition according to the existing patents.

21 Claims, 1 Drawing Sheet

*FIG. 1*

CYCLOSPORIN-CONTAINING MICROEMULSION PRECONCENTRATE COMPOSITION

FIELD OF THE INVENTION

The present invention is related to a microemulsion preconcentrate composition comprising cyclosporin as an active component, alkyl ester of polycarboxylic acid as a lipophilic solvent, oil and surfactant.

BACKGROUND OF THE INVENTION

Cyclosporin is a high molecular peptide compound consisting of 11 amino acids which achieves its potent immunosuppressive activity by inhibiting the growth and differentiation of T cells. There are many cyclosporins such as cyclosporin A, B, C, D, G, etc. depending on the structure of constituent amino acids, but cyclosporin A is preferably used in the clinical field since its pharmacological activity and clinical indication and effectiveness are well established in the art. Cyclosporin was found in Tolypocladium inflatum gams by Borel et al. in 1976, and developed as antibiotics at first. After it was found during the safety test that cyclosporin inhibits the growth of lymphocytes, cyclosporin has become the focus of the world's attention as the only immunosuppressant which can specifically affect only lymphocytes, and made the technical development in the organ transplantation possible.

Cyclosporin has a unique structure, which is a cyclic oligopeptide consisting of 11 amino acids. The seven amino acids of cyclosporin are N-methylated. The four remaining protonated nitrogen atoms can form intermolecular hydrogen bonds with carbonyl groups, which contribute substantially to the rigidity of the cyclosporin skeleton. Therefore, it has a remarkably hydrophobic property, and is relatively insoluble in water (0.04 mg/ml at 25° C.). Due to such a low water-solubility of cyclosporin, the bioavailability of cyclosporin is known as be 30% or less. It was reported that the absorption of such an insoluble compound is greatly influenced by bile juice secretions, the amount of fat in food etc. In case of cyclosporin, it has been reported that differences in absorption between individuals are as great as about 5~50 %. When cyclosporin is administered for a long time, it shows renal toxicity, liver toxicity, etc. The renal side effects comprise a reduction of glomerular filtration, an increase in proximal renal tubular reabsorption and chronic progressive deterioration of nephron.

Since cyclosporin has a large dosage unit and a narrow therapeutic index as well as said properties, and the condition of patient to be treated with cyclosporin is generally unstable, it is very difficult to establish an optimum drug dosage regimen for survival of transplanted patient through maintenance of efficient and constant blood concentration which can prohibit side effects and rejection. Numerous studies have been conducted to overcome the said properties and to develop an improved pharmaceutical formulation. Such studies have mainly concentrated on the means, which are used to solubilize cyclosporin. Typical examples include the uses of microspheres, or mixed solvent systems consisting of vegetable oil and surfactant, the formations of powdery composition using adsorption, inclusion complexes, solid dispersions, and other numerous formulations. An oral preparation containing cyclosporin as the primary active ingredient has been commercialized in solution form or a soft capsule formulation. The preparation uses a mixed vehicle consisting of vegetable oil, surfactant and solvent to solubilize cyclosporin, but did not overcome the cyclosporin properties, that is, low bioavailability of cyclosporin and large individual difference thereof. Therefore, the preparation has many problems in the clinical use.

Microemulsions were first reported by J. H. Schulman in 1943 and have, since then, been mainly studied for application of cosmetics and as carrier of insoluble drugs. A microemulsion comprises two or more immiscible liquid materials together with surfactant like emulsion, but is a thermodynamically stable and optically transparent unlike emulsion. And the microemulsion has very low surface tension and small particle size of less than 100 nm, which together result in high absorption and permeation properties of drug delivered by microemulsion. The microemulsion is, especially, very useful in solubilization and absorption improvement of insoluble drugs. However, since formation of a microemulsion requires a lot of surfactant, severe mucosal irritation caused by the microemulsion preparation, and the volume of dosage becomes large. In medical field, microemulsions have thus been utilized only for preparations, which are applied to the skin such as preparations for hair, detergents, etc.

In case of cyclosporin as the relative insoluble drug, U.S. Pat. No. 4,388,307 discloses an oral liquid preparation, which includes oil, surfactant, and ethanol as the hydrophilic solvent. This preparation is a microemulsion preconcentrate and, therefore, must be diluted with water before it is administered orally. That makes the patient compliance bad, and makes the control of the exact dosage difficult. Since it is also uncomfortable to carry, it is impossible to actually administer to a patient who must undergo cyclosporin therapy for the remaining period of his life.

In order to remove said disadvantages of liquid preparations, the microemulsion preconcentrate formulated in the form of soft capsule has been developed. The microemulsion preconcentrate comprises drug, hydrophilic solvent, surfactant and oil with appropriate mixing ratio, and can form the microemulsion spontaneously dissolving in the outer phase such as water and intestinal fluid. However, the hydrophilic solvent used as essential component of microemulsion preconcentrate permeates the gelatin shell of the capsule to volatilize, and also soften the gelatin shell. Those induced the stability problem of the soft capsules.

In case of the cyclosporin soft capsule containing ethanol as its hydrophilic component, this capsule preparation must contain a large amount of ethanol to solubilize the cyclosporin. However, since ethanol permeates the gelatin shell of the capsule to volatilize even at normal temperature, the content of ethanol is reduced in the course of time. As a result, when the capsules are stored at low temperatures or at normal temperatures for long period, the crystallization of cyclosporin may be caused. The composition change results in a great variation in the bioavailability of cyclosporin and, therefore, it is impossible to obtain a desired therapeutic effect reliably and reproducibly. In an effort to prevent the volatilization of ethanol from the soft capsule preparations during storage, the soft capsules are enclosed in a special packaging material, such as aluminum blister packaging. However, the problem of great variation of cyclosporin bioavailability is still remained in spite of using said special packaging since it is impossible to completely prevent the change of ethanol content in the course of time. Using said special packaging might contribute to an increase of the manufacturing cost and medicinal fee.

To improve the said disadvantages of the use of ethanol as hydrophilic cosurfactant, methods using non-ethanol component as hydrophilic cosurfactant have also been proposed.

U.S. Ser. No. 5,342,625 discloses the soft capsule preparation formulated from microemulsion concentrate which solves the said problems. This patent discloses a pharmaceutical composition in the form of microemulsion concentrate in which a pharmaceutically acceptable $C_{15}$ alkyl or tetrahydrofurfuryl di- or partial- ether of a low molecular mono- or poly- oxy-alkanediol, for example, diethyleneglycol monoethyl ether (e.g. Transcutol), tetrahydrofurfurylalcohol polyethylene glycol ether (e.g. Glycofurol), 1,2-propylene glycol are used as a hydrophilic solvent, and ethanol is used as a hydrophilic co-solvent. However, all the hydrophilic solvents used in this patent are glycols having the alcoholic group (—OH) in their structure. Since such glycols containing —OH group are very hygroscopic, they absorb moisture present in atmosphere and further have a high permeability to gelatin shell. It is, therefore, very difficult to formulate a composition containing such a glycolic cosurfactant into a soft capsule preparation. In encapsulating and first drying steps at the time of preparing soft capsules, particularly, water present in the capsule shell is absorbed into the capsule content by the amount corresponding to 20% of the hygroscopic solvent to cause the change in constitutional ratio of the composition. In drying step of those, water is distributed again into the gelatin shell and volatilized from inside of capsule to outside of that through the capsule shell. The composition materials of capsule content migrate also to capsule shell along with water. Therefore, the constitutional ratio of the composition according to this patent is greatly changed, and the change of the preparation appearance from said phenomena makes the capsule production yield decreased.

The said hydrophilic solvents used in the formulation disclosed by the above U.S. patent have, furthermore, the softening effect for the gelatin shell of capsule, and induce the pharmaceutical problem that the stability of the appearance of gelatin capsule is greatly reduced. This problem becomes even more serious when a material used as a plasticizer for gelatin, for example, propylene glycol, glycerin; etc. is used as a hydrophilic solvent. The use of propylene glycol as the main solvent is, therefore, limited highly. Propylene glycol can be used generally in approximately 5% or less of capsule contents, and may be used in approximately 10% or less together with a hardening agent for gelatin shell at the most. The appearance stability of the gelatin shell is greatly reduced when propylene glycol is used in the amount of exceeding said limits as the content of soft capsule.

Korean Patent Application No. 94-13945 discloses a cyclosporin-containing composition to be formulated in soft capsule (trade name: Neoplanta®) that uses dimethylisosorbide as the hydrophilic cosurfactant for mitigating such disadvantages. This patent describes that since dimethylisosorbide used as the hydrophilic solvent has substantially no permeability to the gelatin shell in comparison to the hydrophilic cosurfactants used in the prior art, the soft capsule preparation using dimethylisosorbide provides some advantages that it does not show the change in appearance of the capsule and content of the ingredients.

Dimethylisosorbide, which is marketed under the trade name Arlasolve®, i.e., 1,4:3,6-dianhydro-2,5-dimethyl-D-glucitol, is a solvent, which has been generally used as a percutaneous absorption enhancer only for topical pharmaceutical ointments or cosmetics such as lotions.

As mentioned above, a conventional microemulsion requires more quantity of surfactant than a general emulsion does and therefore, in case of a drug which is continuously administered to the patient during his whole life after organ transplantation, for example, cyclosporin, the toxicity due to long term administration of solvent and surfactant used in the preparation of the microemulsion must be considered. In this connection, the $LD_{50}$ value of dimethylisosorbide is 5.63 ml/kg (rat, per oral). In case of the organic solvent of which the toxicity has been relatively well known, the $LD_{50}$ (rat, per oral) value of each solvent is as follows: acetonitrile 3.8 g/kg, acetone 10.7 ml/kg, benzene 3.8 ml/kg, toluene 7.53 g/kg, isopropanol 5.8 g/kg and butanol 4.36 g/kg. It is expected that the long-term oral administration of the composition containing dimethylisosorbide may cause problems. Furthermore, the pharmaceutical problems were not improved highly by the use of dimethylisosorbide, since dimethylisosorbide still has the properties, the reactivity with gelatin shell of soft capsule and the volatility and shows the limit as hydrophilic solvent.

U.S. Ser. No. 5,583,105 discloses the oral multiple emulsion comprising cyclosporin in which ethanol and tocopheryl polyethylene glycol 1000 succinate, that is a surfactant, are used as essential vehicle, and oils or alkyl esters of polycarboxylic acid are used as lipophilic or amphiphilic solvent. This patent describes that alkyl esters of polycarboxylic acid can be used selectively instead of oil, and this patent, in particular, employed acetyl triethyl citrate for formulation of cyclosporin. However, ethanol, which is a hydrophilic and volatile solvent, was also used essentially to constitute the cyclosporin formulation. As mentioned above, the cyclosporin preparations using ethanol for the solubilization of cyclosporin show the problem of pharmaceutical stability, such as ethanol volatilization through the gelatin shell of capsule, during the storage. Tocopheryl polyethylene glycol 1000 succinate, which was used as a surfactant in this patent, is a product from esterification of tocopheryl acid succinate with polyethylene glycol, and liberates tocopherol after being absorbed into the body. This patent discloses that free tocopherol can reduce the renal toxicity. However, it does not yet have been verified, and that there could be a drug interaction between tocopherol and cyclosporin for a long therapy and free tocopherol, which may be absorbed in the body exceeding the usual dose. The lipid-soluble vitamins, such as tocopherol, induce the adverse side effect by accumulation in the body.

As mentioned above, the microemulsion preconcentrates according to prior arts have hydrophilic solvent, oil and surfactant as essential and primary composition. In case of formulation of those microemulsion preconcentrates as soft capsule, it has been known generally that hydrophilic solvent reacts with gelatin shell of soft capsule to soften the shell, and volatilizes through the gelatin shell, and that said phenomena induce the serious problem of preparation stability. There was a try to improve the those disadvantage using dimethylisosorbide as new hydrophilic solvent, but this material has the limit as a primary vehicle because of toxicity thereof and still has the disadvantage of hydrophilic solvent.

SUMMARY OF THE INVENTION

The present inventors have studied to develop the cyclosporin-containing composition, which compensates for the disadvantages involved in the various pharmaceutical preparations of the prior art and is suitable for the formulation into the soft capsule. The present inventors developed the new cyclosporin-containing microemulsion preconcentrate, which comprises lipophilic solvent, surfactant and oil, using lipophilic solvent instead of hydrophilic solvent, which causes in disadvantage of pharmaceutical stability. It was identified that the microemulsion preconcentrate using lipophilic solvent instead of hydrophilic solvent can overcome the various problems of prior arts and thus the present invention was completed.

BRIEF DESCRIPTION OF THE DRAWINGS

For a thorough understanding of the nature and objects of the invention, reference should be had to the following detailed description taken in connection with the accompanying drawings in which.

DETAILED DESCRIPTION OF THE INVENTION

The present invention relates to a cyclosporin-containing microemulsion preconcentrate composition that comprises (1) cyclosporin as an active ingredient; (2) alkyl ester of polycarboxylic acid and/or carboxylic acid ester of polyols as a lipophilic solvent; (3) oil; and (4) surfactant.

The first essential component of the cyclosporin-containing microemulsion preconcentrate composition according to the present invention is cyclosporin as an active ingredient. Cyclosporin A is preferred.

The second essential component of the composition according to the present invention is a lipophilic solvent. The lipophilic solvent, which is used in the composition according to the present invention to overcome the disadvantage of hydrophilic solvent, is at least one member selected from alkyl esters of polycarboxylic acid.

The alkyl esters of polycarboxylic acid that can be used in the composition according to the present invention are the products from esterification of polycarboxylic acid having carboxylic groups of 2~10 with $C_1$~$C_{10}$ alcohols, and preferred the products from esterification of polycarboxylic acid having carboxylic groups of 3~5 with $C_1$~$C_{10}$ alcohols.

The carboxylic acid esters of polyols that can be used in the composition according to the present invention are the products from esterification of polyols having hydroxyl groups of 2~10 with $C_2$~$C_{11}$ carboxylic acids, and preferred the products from esterification of polyols having hydroxyl groups of 3~5 with $C_2$~$C_{11}$ carboxylic acids.

The alkyl ester of polycarboxylic acid and/or carboxylic acid ester of polyols used as lipophilic solvent in the composition according to the present invention are odorless and colorless oils in liquid state, and have high boiling point of more than 250° C. They does not volatilize at the condition of high temperature during the procedure for soft capsule preparation as well as in the storage state of room temperature, and therefore, they can insure the stability of preparation comprising them. Moreover, said lipophilic solvent does not show such severe hygroscopic property as glycols show, does not dissolve the gelatin shell, and does not induce the compositional change due to non-volatile and non-permeable for gelatin shell. Said alkyl esters of polycarboxylic acid and or carboxylic acid ester of polyols are lipophilic solvent, which can be applied to the solubilization of insoluble drug such as cyclosporin, and do not induce the problem of preparation stability at the time of preparation and storage of the product.

The alkyl esters of polycarboxylic acid that can be used preferably in the composition according to the present invention comprise triethyl citrate, tributyl citrate, acetyltributyl citrate, acetyltriethyl citrate, etc. The carboxylic acid esters of polyols that can be used preferably in the composition according to the present invention comprise triacetin, etc. They may be used alone or in the mixture of two kinds or more. When the mixture is used, mixing ratio is not particularly limited.

In the cyclosporin-containing microemulsion preconcentrate composition according to the present invention, the ratio of cyclosporin to the lipophilic solvent is preferably in the range of 1:0.1~5, more preferably 1:1~3 by weight.

The cyclosporin-containing microemulsion preconcentrate composition using lipophilic solvent according to the present invention does not show the pharmaceutical disadvantage, which may be induced by hydrophilic solvent, an essential component in composition of the prior art. In an additional remark, the use of the said lipophilic solvent according to the present invention can provide a solubilization effect sufficient for cyclosporin, and also provide many advantages that lipophilic solvent selected in the present invention neither changes the capsule's appearance nor causes precipitation of the active ingredient cyclosporin, because said lipophilic solvent does not react with gelatin shell of soft capsule and is not volatile. Moreover, it reduce the cost of manufacturing to provide an economical effect, and it does not even show any problem of solvent toxicity in the patient administered with said capsule for a long time.

The third essential component of the composition according to the present invention is oil. Oil that can be used in the composition of the present invention comprises vegetable oils; and the esterification products of fatty acids containing in vegetable oils. They may be used alone or in the mixture of two kinds or more. In case of mixture, the selection may be performed only in vegetable oils; only in the esterification products of fatty acids contained in vegetable oils; or in the group consisting of vegetable oils and the esterification products of fatty acids contained in vegetable oils, respectively.

Examples of vegetable oils that can be used in the composition of the present invention are corn oil, borage oil, sesame oil, primrose oil, peanut oil, olive oil, etc. Refined vegetable oils are preferred.

The refined vegetable oils have the high purity and low contents of impurities, and can be controlled the contents of higher unsaturated fatty acids. Therefore, they have been used mainly in the total parenteral nutrition, for the wasting disease such as diabetic nervous disease, rheumatic arthritis, etc., and as vehicle for stabilization of unstable drug. The refined vegetable oils, which passed through refining procedure by chromatography, are more transparent than general oils. Because oxidants such as aldehydes, alcohols, ketones, etc. are removed from them, they are more resistant to oxidation than general oils. And because the polar materials and water contents of them are reduced highly, they have more excellent solubilization effect for drug than general oils. The commercial refined vegetable oils generally have peroxide value of 0.5 or less than, anisidine value of 0.2~0.5, and acid value of 0.1~1.0 or less. The commercial refined vegetable oils have various contents of unsaturated fatty acids depending on the kind of vegetable oil. The oil having the proper content of unsaturated fatty acids for the requirement, therefore, may be selected and used.

Examples of the refined vegetable oils, which are preferable oils of the composition according to the present invention, are super-refined corn oil, borage oil, sesame oil, primrose oil, peanut oil and olive oil, which are on the market as trade name Super-refined oil (Croda Co.). The more preferable oil that can be used in the composition according to the present invention is the form that the content of high gamma linolenic acid in the oil is increased in more than 50%, and example of that oil is concentrated borage oil of trade name Crossential (Croda Co.).

As another oil component that can be used in the composition according to the present invention, the esterification products of fatty acids comprise i) the product from esterification of fatty acid with glycerin; ii) the product from esterification of fatty acid with monohydric alcohol; and iii) the product from esterification of fatty acid with triacetin. Said fatty acids comprise high, medium and low chain fatty acids.

In the esterification products of fatty acids, at first, the product from esterification of fatty acid with glycerin will be described. These comprises fatty acid triglyceride; di-glyceride of fatty acid; mono-glyceride of fatty acid; mono- and di-glycerides of fatty acid; etc.

As a class of the product from esterification of fatty acid with glycerin, fatty acid triglyceride may be used. $C_8$~$C_{12}$ fatty acid medium chain triglyceride (MCT) is preferred. MCT is prepared by esterification of fatty acid extracted from palm oil with glycerin, and is triglyceride of medium chain fatty acid of which main fatty acids are capric acid (50~80%) and caprylic acid (20~50%). Compared to general oils, MCT provides many advantages. Since MCT is more stable against oxidation and higher density as close value (0.94~0.95) to the density of water than general oil, an emulsion using said medium chain fatty acid is more stable than general emulsions. In addition, due to MCT is less hydrophobic than vegetable oils, it is possible to obtain a higher concentration of the active ingredient without a significant increase in the viscosity of the composition when the composition of the present invention is prepared using MCT. This means that MCT is an oil very suitable to the drug of which the dose is great such that the concentration of active ingredient to carrier is as high as 10% and which has very low polarity and therefore, is very slightly soluble in water, for example, cyclosporin. MCT has been commercialized under the trade names Sefol 860, Sefol 870, Sefol 880, Miglyol 810, Miglyol 812, Miglyol 818, etc.

As another class of the product from esterification of fatty acid with glycerin, mono- and di- glyceride could be used. The mono- and di-glycerides mean the form of a mixture of glycol mono- and di-esters of a fatty acid. An example of that is mono- & di-glyceride, which the ratio of monoglyceride to total glycerides is at least 40%, preferably at least 90%. Mono- & di-glyceride of which fatty acid is high chain of $C_{16}$~$C_{18}$ may be used preferably. It is more preferable that mono- & di-glyceride contains a monoglyceride of $C_{18}$ fatty acid as its main component. Such a compound has been commercialized under the trade name GMO AVI (Croda Co.), ATMOS 300 (ICI Co.), GMOrphic-80 (Eastman Co.), etc.

In the esterification products of fatty acids, at second, the product from esterification of fatty acids with monohydric alcohol will be described. There are ethyl oleate, ethyl linoleate, isopropyl palmitate, isopropyl myristate, etc.

In the esterification products of fatty acids, at third, the product from esterification of fatty acids with triacetin will be described. These comprise; di-acetylated monoglyceride; mono- and di-acetylated monoglycerides; etc. Diacetylated monoglyceride of $C_{14}$~$C_{20}$ fatty acid is preferred. Said diacetylated monoglyceride is the product from esterification of edible oils with triacetin. Said diacetylated monoglyceride is used as additive in foods and as plasticizer in medicines, and has been commercialized under the trade name Mivacet 9-40, Mivacet 9-45, etc.

Each mixing combinations of said various oils may further comprise unsaturated higher fatty acids of proper quantity for controlling of cyclosporin absorption. Examples of such fatty acids are oleic acid, linoleic acid, etc.

In the cyclosporin-containing microemulsion preconcentrate composition according to the present invention, the ratio of cyclosporin to oil component is preferably in the range of 1:0.1~5, more preferably 1:1~3 by weight.

The fourth essential component of the composition according to the present invention is a surfactant. Any pharmaceutical acceptable surfactant may be used, provided it is miscible with both the oil and the lipophilic solvent components to form an emulsion under mild stirring in the external phase and can adjust the particle diameter in the inner phase to 100 nm or below by controlling the constitutional ratio thereof. Surfactants which may be used for this purpose have preferably HLB value of 1~20, and there are examples of them as following:

i) Reaction products of natural or hydrogenated vegetable oils and ethylene glycol; i. e., polyoxyethylene glycolated natural or hydrogenated vegetable oils: for example polyoxyethylene glycolated natural or hydrogenated castor oils. Surfactants commercialized under the trade names Cremophor RH40, Cremophor RH60, Cremophor EL and Nikkol may be used in the composition according to the present invention. Cremophor RH40 and Cremophor EL are preferred.

ii) Polyoxyethylene sorbitan fatty acid esters: e.g. mono- and tri-lauryl, palmityl, stearyl and oleyl esters; e.g. products of the trade name "Tween", which includes polyoxyethylene (20) sorbitan mono-laurate (Tween 20), polyoxyethylene (20) sorbitan mono-palmitate (Tween 40), polyoxyethylene (20) sorbitan mono-oleate (Tween 80), etc. depending on the kind of fatty acid. Tween 20 and Tween 40 can be used preferably in the composition according to the present invention.

iii) Polyoxyethylene fatty acid esters: for example, polyoxyethylene stearic acid esters of the type known and commercially available under the trade name Myrj as well as polyoxyethylene fatty acid esters known and commercially available under the trade name "Cetiol HE".

iv) Polyoxyethylene-polyoxypropylene co-polymers: e.g. of the type known and commercially available under the trade names "Pluronic" and "Emkalyx".

v) Polyoxyethylene-polyoxypropylene block co-polymers: e.g. of the type known and commercially available under the trade name "Poloxamer".

vi) Dioctylsuccinate, dioctylsodiumsulfosuccinate, di-[2-ethylhexyl]-succinate or sodium lauryl sulfate.

vii) Phospholipids, in particular lecithins: especially, soybean lecithin.

viii) Bile salts: e.g. alkali metal salts, for example sodium taurocholate.

ix) Trans-esterification products of natural vegetable oil triglycerides and polyalkylene polyols; e.g. of the type known and commercially available under the trade name Labrafil. Specially, Labrafil M 1944 CS, Labrafil WL 2609 BS, Labrasol, etc. can be used preferably in the composition according to the present invention.

x) Mono-, di-and mono/di-glycerides: especially esterification products of caprylic or capric acid with glycerol.

xi) Sorbitan fatty acid esters: for example, of the type known and commercially available under the trade name Span.

xii) Pentaerythritol fatty acid esters and polyalkylene glycol ethers: for example pentaerythrite-dioleate, -distearate, -monolaurate, -polyglycol ether and -monostearate as well as pentacrythrite-fatty acid esters.

xiii) Sterols and derivatives thereof, for example cholesterols and derivatives thereof, in particular phytosterols: e.g. products comprising sitosterol, campesterol or stigmasterol, and ethylene oxide adducts thereof, for example soya sterols and derivatives thereof, such as known under the trade name Generol.

Surfactants that may be used more preferably in the composition according to the present invention are polyoxyethylene glycolated natural or hydrogenated vegetable oils; trans-esterification products of natural vegetable oil triglycerides and polyalkylene polyols; and lecithins.

Said surfactants can be used alone or in the mixture of two kinds or more. In the cyclosporin-containing microemulsion preconcentrate composition according to the present invention, the ratio of cyclosporin to surfactant preferably in the range of 1:2~10, more preferably 1:3~8 by weight.

In the cyclosporin-containing microemulsion preconcentrate composition according to the present invention, said four essential components should be present preferably in the mixing ratio of cyclosporin: lipophilic solvent: surfactant: oil=1:0.1~5:2~10:0.1~5, and more preferably in the mixing ratio of cyclosporin: lipophilic solvent: surfactant: oil=1:1~3:3~8:1~3, on the basis of weight.

The composition according to the present invention is characterized in that it dissolves in an external phase such as water, artificial gastric fluid and artificial intestinal fluid by controlling the mixing ratio of the components thereby to get the microemulsion form of inner phase diameter of 100 nm or below.

The cyclosporin-containing composition according to the present invention may further comprise any pharmaceutically acceptable additives as needed. Examples of said additives include antioxidant (e.g., tocopherol, butylated hydroxyanisole (BHA), etc.), viscosity control agent, dissolution control agent, flavor (e.g., peppermint oil, etc.), preservatives (e.g., benzyl alcohol, parabens, etc.) and coloring agents.

For clinical use, the composition according to the present invention can be formulated as the dosage form of a soft capsule, a hard capsule sealed with a gelatin banding at the conjugated portion, or an oral liquid preparation to administer into patient orally. The composition of the present invention can be formulated into soft capsules by the conventional method, for example, by dissolving cyclosporin in lipophilic solvent component under mild warming, adding the oil and surfactant components to the resulting solution, uniformly mixing the constituents, then, if necessary, adding pharmaceutically acceptable additives, and finally formulating the resulting mixture, i.e. the composition according to the present invention, into soft capsules using a machine for preparing soft capsule.

Microemulsion preconcentrate prepared with lipophilic solvent instead of hydrophilic solvent according to the present invention, especially used as the dosage form of soft capsule, yields higher blood concentration of cyclosporin than commercial product of cyclosporin soft capsule, and the resultant capsule do not exhibit any change of composition with time due to volatilization and permeation of the components. Moreover, it reduces the manufacturing cost and the toxicity of solvent, which may make a problem in long-term therapy. The cyclosporin-containing composition according to the present invention, therefore, represents and improves over cyclosporin soft capsules of the prior art.

PREFERRED EMBODIMENTS OF THE INVENTION

The present invention is described in more detail by Examples and Experiment as shown below but is not confined to said scopes.

EXAMPLE 1

Cyclosporin soft capsule for oral administration 50 g of cyclosporin as an active ingredient was dissolved in 100 g of triethyl citrate as a lipophilic solvent component with stirring and heating. 100 g of Miglyol 810 and 50 g of Mivacet 9-45 as oil components, and 200 g of Cremophor RH 40 as an surfactant component were added to obtain the mixture, which was stirred until a homogeneous solution was formed. The resulting composition was poured to a machine for preparing soft capsules and then encapsulated according to conventional methods for producing soft capsules. Each capsules contained 50 mg of cyclosporin.

The soft capsule preparations of Examples 1-A to 1-D, having the compositions given in the following Table 1, were prepared according to said method.

TABLE 1

| Components | | Composition (mg/capsule) | | | |
| --- | --- | --- | --- | --- | --- |
| | | Example 1-A | Example 1-B | Example 1-C | Example 1-D |
| Active ingredient | Cyclosporin | 50.0 | 50.0 | 50.0 | 50.0 |
| Lipophilic solvent | Triethyl citrate | 150.0 | | | 50.0 |
| | Triacetin | | 125.0 | | |
| | Acetyl-triethyl citrate | | | 150.0 | 100.0 |
| Surfactant | Cremophor RH 40 | 225.0 | 175.0 | 180.0 | 90.0 |
| | Labrafil | | 75.0 | 50.0 | 150.0 |
| Oil | Miglyol 812 | 125.0 | 125.0 | 110.0 | 110.0 |
| Total | | 550.0 | 550.0 | 540.0 | 550.0 |

EXAMPLE 2

Cyclosporin soft capsule for oral administration

The soft capsule preparations of Examples 2-A to 2-F, having the compositions given in the following Table 2, were prepared according to the method of Example 1.

TABLE 2

| Components | | Composition (mg/capsule) | | | | | |
|---|---|---|---|---|---|---|---|
| | | Example 2-A | Example 2-B | Example 2-C | Example 2-D | Example 2-E | Example 2-F |
| Active ingredient | Cyclosporin | 50.0 | 50.0 | 50.0 | 50.0 | 50.0 | 50.0 |
| Lipophilic solvent | Triethyl citrate | 120.0 | | | 80.0 | | |
| | Triacetin | | 140.0 | | | | 50.0 |
| | Tributyl citrate | | | | | 40.0 | |
| | Acetyltributyl citrate | | | 40.0 | | 40.0 | |
| | Acetyltriethyl citrate | 20.0 | 10.0 | | 80.0 | | 40.0 |
| Surfactant | Cremophor RH 60 | 200.0 | 210.0 | 220.0 | 150.0 | 70.0 | |
| | Tween 20 | | 20.0 | | 70.0 | 150.0 | 220.0 |
| Oil | GMOrphic 80 | 50.0 | 80.0 | | 30.0 | 30.0 | 30.0 |
| | Mivacet 9-45 | 50.0 | | 50.0 | | 50.0 | |
| | Sefol 880 | 50.0 | 70.0 | 80.0 | 100.0 | 50.0 | 100.0 |
| Total | | 540.0 | 580.0 | 520.0 | 480.0 | 480.0 | 490.0 |

EXAMPLE 3

Cyclosporin soft capsule for oral administration

The soft capsule preparations of Examples 3-A to 3-F, having the compositions given in the following Table 3, were prepared according to the method of Example 1.

EXAMPLE 4

Cyclosporin soft capsule for oral administration

The soft capsule preparations of Examples 4-A to 4-F, having the compositions given in the following Table 4, were prepared according to the method of Example 1.

TABLE 3

| Components | | Composition (mg/capsule) | | | | | |
|---|---|---|---|---|---|---|---|
| | | Example 3-A | Example 3-B | Example 3-C | Example 3-D | Example 3-E | Example 3-F |
| Active ingredient | Cyclosporin | 50.0 | 50.0 | 50.0 | 50.0 | 50.0 | 50.0 |
| Lipophilic solvent | Triethyl citrate | 80.0 | | 80.0 | | | |
| | Triacetin | | 110.0 | | | | |
| | Tributyl citrate | 30.0 | 20.0 | | 120.0 | | |
| | Acetyltributyl citrate | 10.0 | | 40.0 | | 100.0 | |
| | Acetyltriethyl citrate | 20.0 | 10.0 | | | | 150.0 |
| Surfactant | Cremophor EL | 150.0 | 210.0 | 220.0 | | 70.0 | |
| | Tween 20 | | 20.0 | | 150.0 | 150.0 | |
| | Lecithin | 60.0 | 30.0 | | 30.0 | 30.0 | 30.0 |
| | Labrafil | 50.0 | | 50.0 | | 50.0 | 150.0 |
| Oil | Super-refined olive oil | 150.0 | 100.0 | 120.0 | 130.0 | 100.0 | 130.0 |
| Total | | 600.0 | 550.0 | 560.0 | 480.0 | 550.0 | 510.0 |

TABLE 4

| Components | | Example 4-A | Example 4-B | Example 4-C | Example 4-D | Example 4-E | Example 4-F |
|---|---|---|---|---|---|---|---|
| Active ingredient | Cyclosporin | 50.0 | 50.0 | 50.0 | 50.0 | 50.0 | 50.0 |
| Lipophilic solvent | Triethyl citrate | 100.0 | | 120.0 | | 50.0 | |
| | Acetyltributyl citrate | | 130.0 | | | 20.0 | 100.0 |
| | Acetyltriethyl citrate | 30.0 | 20.0 | | 130.0 | 30.0 | |
| Surfactant | Cremophor RH 40 | 250.0 | 210.0 | 220.0 | 180.0 | 250.0 | 200.0 |
| Oil | Miglyol 812 | 120.0 | 90.0 | 70.0 | | 30.0 | |
| | Mivacet 9-40 | | 20.0 | | 100.0 | 25.0 | |
| | GMOrphic 80 | 30.0 | 10.0 | | 15.0 | 10.0 | |
| | Super-refined corn oil | | | 10.0 | | 30.0 | |
| | concentrated borage oil | | | | 10.0 | 35.0 | |
| | Super-refined olive oil | | 10.0 | 60.0 | 20.0 | 10.0 | 150.0 |
| | Ethyl linoleate | | | | | 10.0 | |
| Total | | 580.0 | 540.0 | 530.0 | 505.0 | 550.0 | 500.0 |

EXAMPLE 5

Cyclosporin soft capsule for oral administration

The soft capsule preparations of Examples 5-A to 5-E, having the compositions given in the following Table 5, were prepared according to the method of Example 1.

TABLE 5

| Components | | Example 5-A | Example 5-B | Example 5-C | Example 5-D | Example 5-E |
|---|---|---|---|---|---|---|
| Active ingredient | Cyclosporin | 50.0 | 50.0 | 50.0 | 50.0 | 50.0 |
| Lipophilic solvent | Triethyl citrate | 100.0 | | 80.0 | | 50.0 |
| | Acetyltriethyl citrate | 30.0 | 120.0 | | 120.0 | 40.0 |
| Surfactant | Cremophor RH 40 | 180.0 | 210.0 | 220.0 | 220.0 | 250.0 |
| Oil | Miglyol 812 | 100.0 | 80.0 | 80.0 | | 70.0 |
| | Mivacet 9-40 | | 20.0 | | 110.0 | 20.0 |
| | GMOrphic 80 | 10.0 | 30.0 | | 20.0 | 20.0 |
| | Super-refined peanut oil | | | 40.0 | | 20.0 |
| | Isopropyl myristate | 30.0 | | 30.0 | 10.0 | |
| Antioxidant | Tocopherol | 0.7 | 1.0 | 3.0 | 1.5 | 2.0 |
| Total | | 500.7 | 511.0 | 503.0 | 531.5 | 522.0 |

EXAMPLE 6

Cyclosporin soft capsule for oral administration

The soft capsule preparations of Examples 6-A to 6-D, having the compositions given in the following Table 6, were prepared according to the method of Example 1. These soft capsules contain 100 mg of cyclosporin per capsule.

TABLE 6

| Components | | Example 6-A | Example 6-B | Example 6-C | Example 6-D |
|---|---|---|---|---|---|
| Active ingredient | Cyclosporin | 100.0 | 100.0 | 100.0 | 100.0 |
| Lipophilic solvent | Triethyl citrate | 150.0 | | | 150.0 |
| | Triacetin | 50.0 | 250.0 | 150.0 | 20.0 |
| | Tributyl citrate | | | 50.0 | 20.0 |
| Surfactant | Cremophor RH 40 | 400.0 | 300.0 | 200.0 | 450.0 |
| | Labrafil | | 150.0 | 200.0 | |
| Oil | GMOrphic 80 | 80.0 | | | 30.0 |
| | Mivacet 9-45 | 80.0 | 50.0 | | 30.0 |
| | Sefol 880 | 140.0 | 150.0 | 150.0 | 170.0 |
| | Super-refined oil | | 50.0 | 150.0 | 50.0 |
| Total | | 1000.0 | 1050.0 | 1000.0 | 1020.0 |

EXAMPLE 7

Cyclosporin hard capsule for oral administration

The cyclosporin-containing microemulsion preconcentrate compositions were prepared in the same compositions and methods with Examples 1 to 6, and then were filled in hard gelatin capsules. The conjugated portion of the hard capsules was sealed with gelatin banding to produce hard capsules containing 50 or 100 mg of cyclosporin per capsule.

EXPERIMENTAL EXAMPLE 1

To compare the pharmacological effect of the cyclosporin-containing microemulsion preconcentrate composition according to the present invention with that of commercial product prepared according to prior art, the bioavailability comparison experiment was performed using dogs as follows. The soft capsules of Examples 6-A to 6-D were used as test preparations according to the present invention, and Sandimmun® 100-mg soft capsules, which are commercial product, were used as a comparative preparation.

In this bioavailability study, fifteen male dogs, weighing 11.0~15.0 kg, were used, and each groups was consisted with three dogs. No food except water was supplied to dogs for 18 h prior to drug administration. The dogs were given each soft capsules preparations with the dose of cyclosporin 100 mg per a dog, and then 50 ml of water was administered immediately. After 4 h from drug administration, food was provided. Venous blood samples of 2 ml was withdrawn in the cephalic vein before drug administration for baseline cyclosporin levels, and at schedule time intervals after dosing. Blood samples were frozen under −18° C. until assay. Blood concentrations of cyclosporin were analyzed by RIA (radioimmunoassay) method.

The dog whole blood cyclosporin concentration vs. time curves of each preparations are presented in FIG. 1, and the pharmacokinetic parameters calculated from the experimental data are given in the following Table 7.

TABLE 7

Bioavailability of the test preparation of the present invention and the comparative preparation

| Pharmaco-kinetic parameters | Test preparations | | | | |
| --- | --- | --- | --- | --- | --- |
| | Example 6-A | Example 6-B | Example 6-C | Example 6-D | Comparative preparation |
| $AUC_{0-24}$ (ng.h/ml) | 6267.12 | 6663.33 | 4341.68 | 5150.13 | 2433.85 |
| $C_{max}$ (ng/ml) | 1210.59 | 1143.26 | 945.17 | 989.60 | 498.57 |
| $T_{max}$ (h) | 1.5 | 2.0 | 2.0 | 1.5 | 1.5 |

Figure 1:
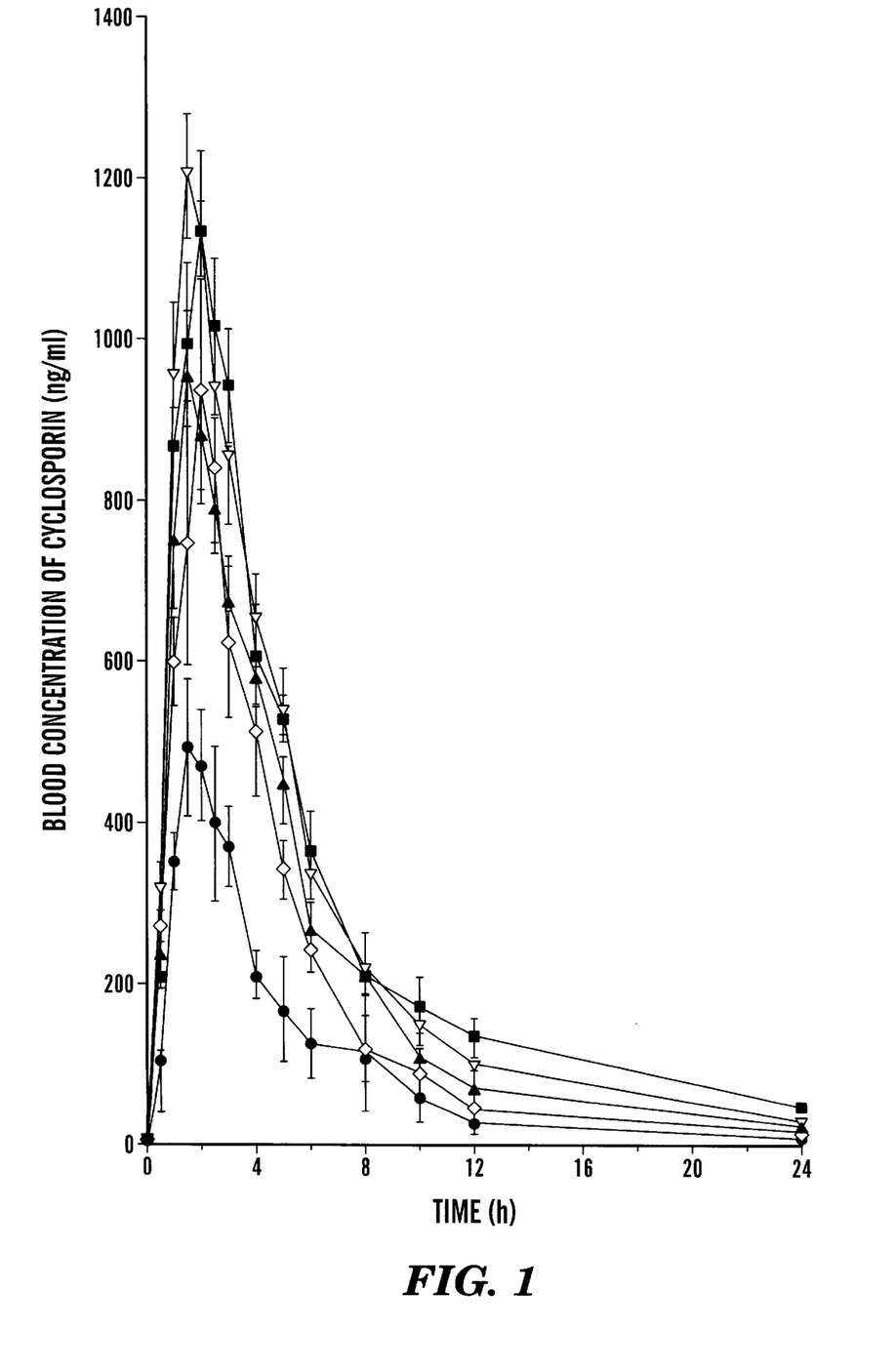
FIG. 1 is blood concentration-time profiles of cyclosporin following the oral administration of cyclosporin commercial product (Sandimmun®: comparative preparation) and cyclosporin-containing pharmaceutical compositions according to the present invention (test preparations) to dogs (●—●, comparative preparation; ▽—▽, test preparation 6-A; ■—■, test preparation 6-B; ◊—◊, test preparation 6-C; ▲—▲, test preparation 6-D).

As can be shown from FIG. 1 and Table 7, the cyclosporin-containing microemulsion preconcentrate compositions using lipophilic solvent according to the present invention showed very larger AUC (area under the curve of cyclosporin blood concentration) as well as higher $C_{max}$ (maximum blood concentration of cyclosporin) than comparative preparation does. Compared with comparative preparation, the AUC of cyclosporin after the oral administration of test preparation 6-A, 6-B, 6-C and 6-D were 2.54, 2.44, 1.81 and 2.12 times, respectively, and, that is, the test preparations showed high absorption pattern.

From the results of Experimental example as mentioned above, it was certified that the composition of the present invention has high bioavailability of two or more times compared with preparation of prior art, and may show the excellent effect of cyclosporin. In addition, the cyclosporin-containing microemulsion preconcentrate composition according to the present invention provide the excellent cyclosporin preparation which can overcome the various disadvantages, that is, forming of cyclosporin precipitation due to solvent evaporation, non-expectable changing of cyclosporin bioavailability induced from drug precipitating, undesirable changing of preparation external appearance, increasing of production cost due to use of special package, etc.

What is claimed is:

1. A cyclosporin-containing pharmaceutical composition, said composition adapted for oral administration as a microemulsion preconcentrate and comprising:

1) a cyclosporin as an active ingredient;

2) a lipophilic solvent chosen from an alkyl ester of polycarboxylic acid and a carboxylic acid ester of polyols;

3) an oil; and 4) a surfactant.

2. A composition according to claim 1, wherein said cyclosporin is cyclosporin A.

3. A composition according to claim 1, wherein said alkyl ester of polycarboxylic acid is at least one member selected from the group consisting of triethyl citrate, tributyl citrate, acetyltributyl citrate, and acetyltriethyl citrate.

4. A composition according to claim 1, wherein said carboxylic acid ester of polyols is triacetin.

5. A composition according to claim 1, wherein said oil is at least one member selected from the group consisting of vegetable oil and/or the esterification product of fatty acid.

6. A composition according to claim 5, wherein said vegetable oil is refined vegetable oils.

7. A composition according to claim 6, wherein said refined vegetable oil is refined-form of corn oil, borage oil, sesame oil, primrose oil, peanut oil and olive oil.

8. A composition according to claim 5, wherein the esterification product of fatty acid contained in vegetable oil is i) the product from esterification of fatty acid with glycerin;

ii) the product from esterification of fatty acid with monohydric alcohol; and iii) the product from esterification of fatty acid with triacetin.

9. A composition according to claim 8, wherein said product from esterification of fatty acid with glycerin is fatty acid triglyceride; and/or mono- and di- glyceride.

10. A composition according to claim 9, wherein said fatty acid triglyceride is a $C_8$~$C_{12}$ fatty acid medium chain triglyceride.

11. A composition according to claim 9, wherein said mono- and di-glyceride is a $C_{16}$–$C_{18}$ fatty acid mono- and di-glyceride.

12. A composition according to claim 8, wherein said product from esterification of fatty acid with monohydric alcohol is at least one member selected from the group consisting of ethyl oleate, ethyl linoleate, isopropyl palmitate and isopropyl myristate.

13. A composition according to claim 8, wherein said product from esterification of fatty acid with triacetin is a $C_{14}$–$C_{20}$ fatty acid diacetylated monoglyceride.

14. A composition according to claim 1, wherein said oil further comprises unsaturated long chain fatty acids.

15. A composition according to claim 1, wherein said surfactant has HLB value of 1~20.

16. A composition according to claim 15, wherein said surfactant is at least one member selected from the group consisting of polyoxyethylene glycolated natural or hydrogenated vegetable oils; polyoxyethylene sorbitan fatty acid esters; polyoxyethylene fatty acid esters; polyoxyethylene-polyoxypropylene co-polymers; polyoxyethylene-polyoxypropylene block co-polymers; dioctylsuccinate, dioctyl sodium sulfosuccinate, di-[2-ethylhexyl]-succinate or sodium lauryl sulfate; phospholipids; bile salts; trans-esterification products of natural vegetable oil triglycerides and polyalkylene polyols; mono-, di- and mono/di-glycerides; sorbitan fatty acid esters; pentaerythritol fatty acid esters and polyalkylene glycol ethers; and sterols and derivatives thereof.

17. A composition according to claim 16, wherein said surfactant is at least one member selected from the group consisting of polyoxyethylene glycolated natural or hydrogenated vegetable oils; trans-esterification products of natural vegetable oil triglycerides and polyalkylene polyols; and lecithins.

18. A composition according to claim 1, wherein said cyclosporin, said lipophilic solvent, said surfactant and said oil component is present in the mixing ratio of 1:0.1~5:2~10:0.1~5 on the basis of weight.

19. A composition according to claim 18, wherein said cyclosporin, said lipophilic solvent, said surfactant and said oil component is present in the mixing ratio of 1:1~3:3~8:1~3 on the basis of weight.

20. A composition according to claim 1, wherein it further comprises at least one species of pharmaceutically acceptable additives selected from the group consisting of antioxidant, viscosity control agent, dissolution control agent, flavor, preservatives and coloring agents.

21. A pharmaceutical formulation comprising the composition according to claim 1, wherein the dosage form is chosen from a soft capsule, a hard capsule sealed with a gelatin banding at the conjugated portion, and an oral liquid preparation.

* * * * *

UNITED STATES PATENT AND TRADEMARK OFFICE
CERTIFICATE OF CORRECTION

PATENT NO. : 6,028,067
DATED : February 22, 2000
INVENTOR(S) : Hong et al.

It is certified that error appears in the above-identified patent and that said Letters Patent is hereby corrected as shown below:

Claim 14, Col. 16, line 49, delete "long chain" and replace with --higher--.

Signed and Sealed this

Thirteenth Day of February, 2001

Attest:

NICHOLAS P. GODICI

Attesting Officer    Acting Director of the United States Patent and Trademark Office